US012089997B2

(12) United States Patent
Heimdal et al.

(10) Patent No.: US 12,089,997 B2
(45) Date of Patent: Sep. 17, 2024

(54) SYSTEM AND METHODS FOR IMAGE FUSION

(71) Applicant: GE Precision Healthcare LLC, Wauwatosa, WI (US)

(72) Inventors: Andreas Heimdal, Oslo (NO); Federico Veronesi, Bologna (IT); Lars Hofsoy Breivik, Oslo (NO)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 48 days.

(21) Appl. No.: 17/644,541

(22) Filed: Dec. 15, 2021

(65) Prior Publication Data

US 2023/0181165 A1    Jun. 15, 2023

(51) Int. Cl.
*A61B 8/08* (2006.01)
*A61B 8/00* (2006.01)
(52) U.S. Cl.
CPC ............ *A61B 8/5261* (2013.01); *A61B 8/463* (2013.01); *A61B 8/466* (2013.01); *A61B 8/469* (2013.01)
(58) Field of Classification Search
CPC ....... A61B 8/5261; A61B 8/463; A61B 8/466; A61B 8/469
See application file for complete search history.

(56) References Cited

U.S. PATENT DOCUMENTS

| 5,706,816 A * | 1/1998 | Mochizuki .......... G01S 15/8993 600/443 |
| 6,725,087 B1 * | 4/2004 | Rubinsky ............... G16H 30/40 128/920 |
| 6,993,171 B1 * | 1/2006 | Choi ..................... G06T 11/001 382/128 |

(Continued)

FOREIGN PATENT DOCUMENTS

| EP | 2680778 B1 | 7/2019 | |
| WO | WO-2012140396 A1 * | 10/2012 | ............. A61B 5/053 |

OTHER PUBLICATIONS

Xie, H. et al., "3D Voxel Fusion of Multi-modality Medical Images in a Clinical Treatment Planning System," Proceedings of the 17th IEEE Symposium on Computer-Based Medical Systems, Jun. 25, 2004, Bethesda, Maryland, 6 pages.

*Primary Examiner* — Joseph M Santos Rodriguez
*Assistant Examiner* — Brooke Lyn Klein
(74) *Attorney, Agent, or Firm* — McCoy Russell LLP

(57) ABSTRACT

Methods and systems are provided for fusing tissue characterization information into ultrasound images. In one example, a method includes obtaining first image data of an anatomical region of interest (ROI) of a patient, the first image data including tissue characterization information and acquired with a first imaging modality; obtaining second image data of the anatomical ROI of the patient, the second image data acquired with a second imaging modality; registering the first image data and the second image data;

(Continued)

adjusting the second image data based on the tissue characterization information and the registration, wherein the adjusting includes filtering, adjusting colorization, adjusting brightness, and/or adjusting material appearance properties of one or more aspects of the second image data; generating a fused image from the adjusted second image data; and outputting the fused image for display and/or storage.

18 Claims, 7 Drawing Sheets
(4 of 7 Drawing Sheet(s) Filed in Color)

(56) References Cited

U.S. PATENT DOCUMENTS

| | | | |
|---|---|---|---|
| 7,889,912 B2 | 2/2011 | Orderud | |
| 8,326,007 B2 | 12/2012 | Langeland et al. | |
| 9,600,879 B2* | 3/2017 | Bystrov | G06T 7/0012 |
| 10,675,006 B2* | 6/2020 | Guracar | A61B 8/5261 |
| 2014/0371774 A1* | 12/2014 | Hwang | A61B 8/54 |
| | | | 606/169 |
| 2015/0326872 A1* | 11/2015 | Lee | G16H 50/20 |
| | | | 382/131 |
| 2016/0317129 A1* | 11/2016 | Seip | A61B 8/488 |
| 2019/0159842 A1* | 5/2019 | Razeto | A61B 6/463 |
| 2019/0336109 A1* | 11/2019 | Pheiffer | G06T 7/37 |
| 2022/0148238 A1* | 5/2022 | He | G01S 7/52036 |
| 2023/0052401 A1* | 2/2023 | Palma | G16H 30/40 |

* cited by examiner

SYSTEM AND METHODS FOR IMAGE FUSION

TECHNICAL FIELD

Embodiments of the subject matter disclosed herein relate to ultrasound imaging, and more particularly, to fusing tissue characterization information with ultrasound data.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In an embodiment, a method includes obtaining first image data of an anatomical region of interest (ROI) of a patient, the first image data including tissue characterization information and acquired with a first imaging modality, obtaining second image data of the anatomical ROI of the patient, the second image data acquired with a second imaging modality, registering the first image data and the second image data, adjusting the second image data based on the tissue characterization information and the registration, wherein the adjusting includes filtering, adjusting colorization, adjusting brightness, and/or adjusting material appearance properties of one or more aspects of the second image data, and generating a fused image from the adjusted second image data; and outputting the fused image for display and/or storage.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various aspects of this disclosure may be better understood upon reading the following detailed description and upon reference to the drawings in which.

DETAILED DESCRIPTION

Figure 1:
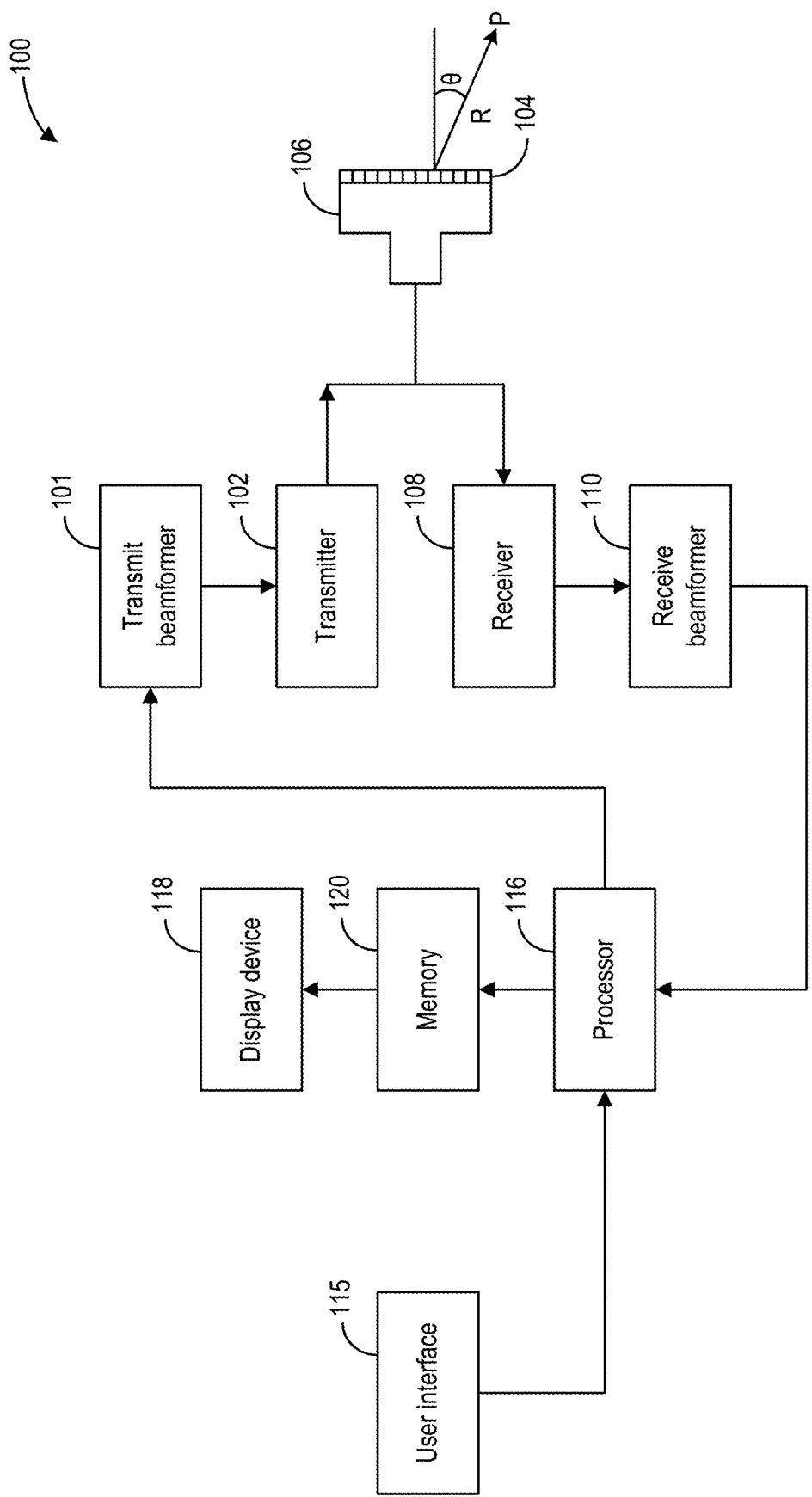
FIG. 1 shows a block diagram of an embodiment of an ultrasound system.

Many techniques have been developed for diagnostic medical imaging over the years. Diagnostic images may be obtained from ultrasound, computed tomography (CT), positron emission tomography (PET), and various other modalities. Some modalities, such as CT, may be used to generate tissue characterization (TC) data. TC data may convey information about various underlying tissues imaged in medical scans, such as differentiating fat from muscle. TC data may be determined from images acquired with certain imaging modalities, such as a computed tomography scan with different types of tissue identified. In CT images, various tissues in the body may be characterized automatically, for example, through the use of Hounsfield (HU) units and/or manually through user highlighting. In some examples, TC data may be presented as a 3D model generated by the TC modality, which may include a 3D CT scan. In addition, 2D images may be generated through either the scans themselves or through various representations of the 3D data.

Ultrasound may also be used to noninvasively produce 3D diagnostic imagery of patients. Ultrasound is commonly employed as a method to image the 3D structural anatomy of the patient. Compared to radiological methods, such as CT, PET, and others, ultrasound imaging has several advantages. Since ultrasound creates images through the echoes of high-frequency sound waves, patients receive no dosage of radiation when undergoing ultrasound scans. Since high or repeated doses of radiation (e.g. x-rays) may pose health risks, repeated CT scans are often not desirable. Contrary to CT, ultrasound may be used continuously to image bodily processes. Bodily processes may be examined in real-time through continuous ultrasound imaging. For example, a series of ultrasound images may be captured to represent a cyclical process, such as the cardiac cycle. Continuous images may also be used during interventional procedures such as ablations or biopsies. Ultrasound images are also commonly used to measure blood flow within a patient's body, since different flow rates of blood may produce different echoes in response to ultrasonic sound waves.

Raw ultrasound data may be gathered through the use of an ultrasound system, which may in turn generate 2D images and/or a 3D rendering of the underlying anatomy. One or more 3D models may represent cyclical bodily processes, real-time data from interventional procedures, or other diagnostic images. The diagnostic images collected from ultrasound may be represented in a variety of ways, including slices and/or renderings of the 3D shape with coloring and/or brightness adjusted according to ultrasound data.

Although ultrasound images may provide a host of useful information to medical professionals, ultrasound data may not provide robust tissue characterization data. Furthermore, ultrasound may have a low spatial resolution, limited by the wavelength of the incident waves. Certain areas of the body may be difficult to image with ultrasound due to attenuation of the sound waves within certain tissues. As mentioned above, tissue characterization data may be instead obtained from a different diagnostic modality, such as CT imaging.

CT scans (and other radiological imaging modalities) may provide more accurate characterizations of the underlying tissues. For example, CT scans may use x-rays to differentiate between tissues by measuring the attenuation of the x-rays. Tissue characterization data may be collected at a higher resolution than the ultrasound imagery and more accurately differentiate between blood, fat, bone, and other tissues.

Medical professionals may find that CT (or other modality) images and ultrasound images are difficult to view simultaneously, and in particular medical professionals may find translating information contained in only one image (e.g., tissue characterization information in CT images) to other images (e.g., ultrasound images) challenging, since the tissue characterization information may have to be (mentally) scaled, rotated, and otherwise transformed appropriately to be applied to the ultrasound images. Such transformation calculations may be performed mentally through the use of correlating notable anatomical structures, which may be mentally difficult to perform, especially considering the 3D context of the images viewed on the 2D screen. Novice users of the imaging systems may find comprehension of side-by-side renderings of anatomical ROIs in two modalities more difficult.

According to embodiments disclosed herein, simultaneous viewing of the ultrasound and TC information (e.g., from CT images/models) may be provided via fusion of the ultrasound and TC information. The fusion may include adjusting aspects of the ultrasound data (e.g., pixels, voxels, or surface points of a 3D model) by filtering, adjusting colorization, adjusting brightness, and/or adjusting material appearance properties of the one or more aspects of the ultrasound image data based on the TC information. This may include, for example, adjusting the coloring and/or brightness of the ultrasound images using the coloring and/or brightness of the TC images (e.g., whether directly or using a transformation to turn a color or brightness of the TC images into a different color or brightness). Using a series of reference points, locations within the ultrasound scans may be identified with locations within a CT scan, for example. Identification of the pixels and/or voxels of the ultrasound and TC information (e.g., CT data) allows for the color and/or brightness of the ultrasound scan's pixels and/or voxels to be adjusted, creating a fused image in the volume of the anatomical ROI imaged by both CT and ultrasound.

Additional ultrasound images may also be collected, allowing the fused volumetric data to be updated according to changes in the underlying anatomy during, for example, the stages of a cardiac cycle. The techniques described herein may be advantageous compared to traditional ultrasound or CT scans alone or side-by-side, since both tissue characterization and 3D model data is available for viewing simultaneously and in the same space, and may thus provide an intuitive way to see blood flow, anatomical structure, tissue characterization, and more in a single image or series of images, which may be updated to reflect the phases of a time-dependent process.

Figure 3:
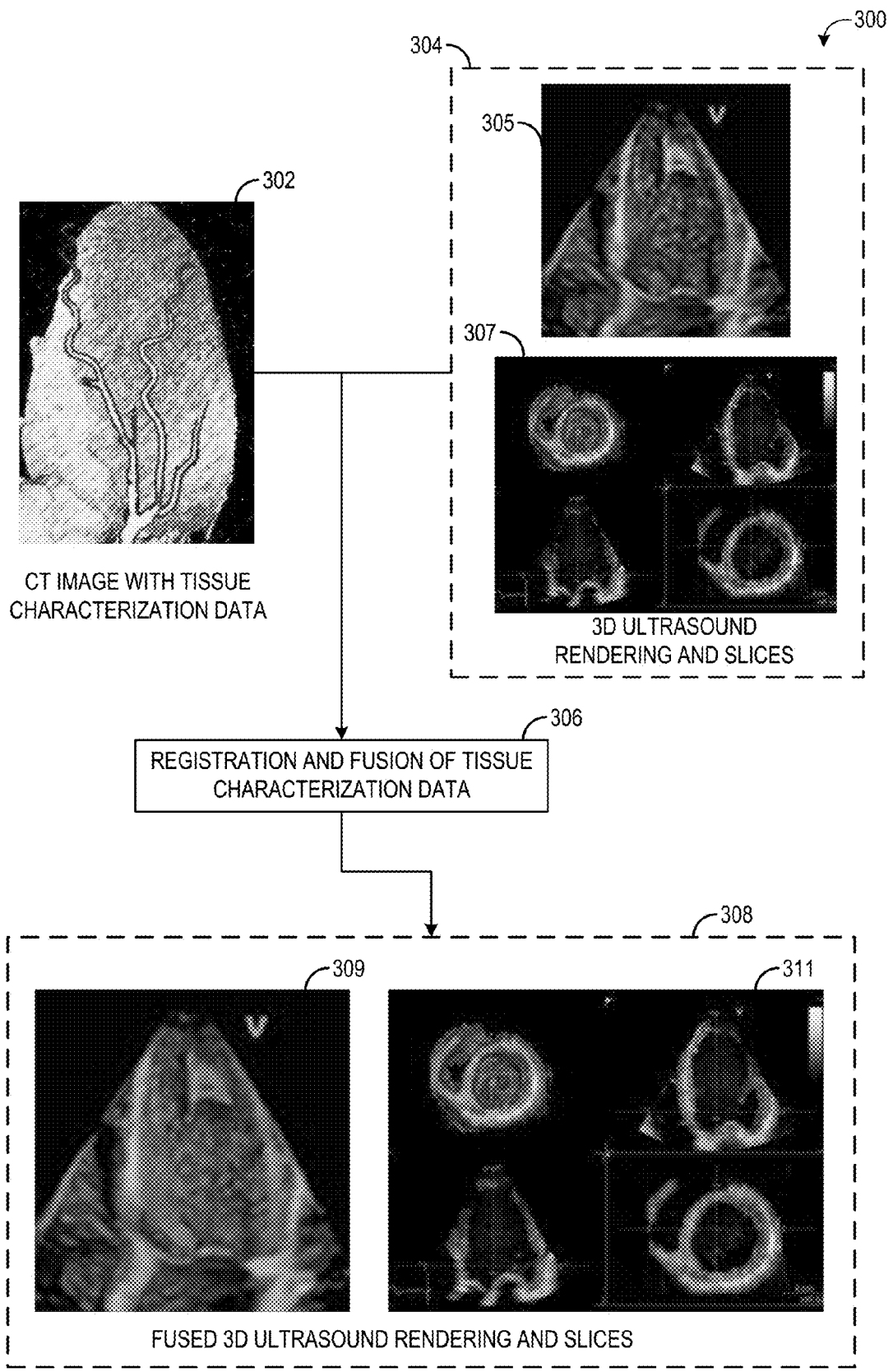
FIG. 3 schematically shows an example process for fusing TC information with still frames of ultrasound images.
Figure 4:
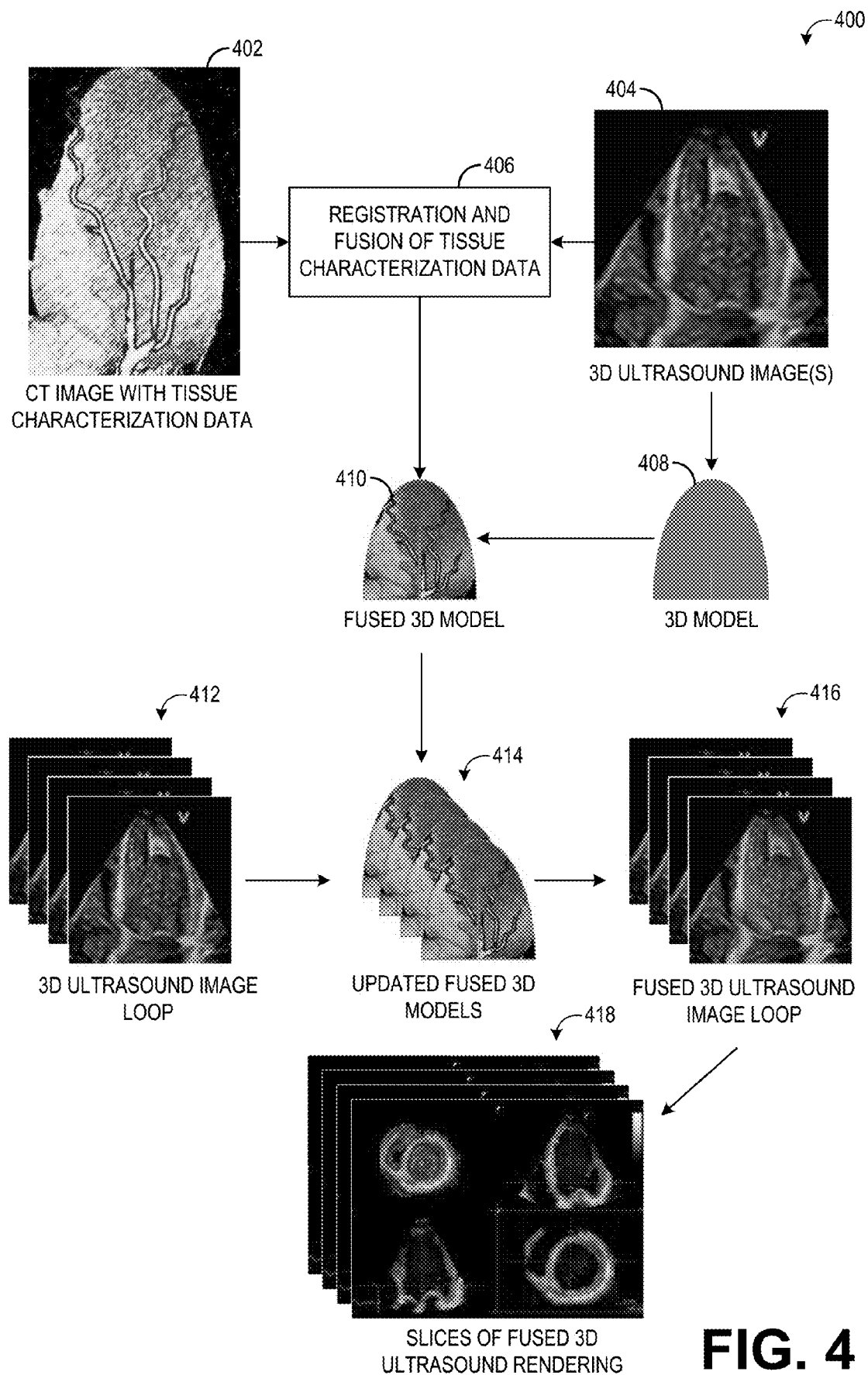
FIG. 4 schematically shows an example process for fusing TC information with ultrasound image loops.

An example ultrasound system including an ultrasound probe, a display device, and an imaging processing system are shown in FIG. 1. Via the ultrasound probe, ultrasound data may be acquired and ultrasound images (which may include 2D images, 3D renderings, and/or slices of a 3D volume) may be displayed on the display device. The ultrasound images may be processed by an image processing system, such as the image processing system of FIG. 2, to include tissue characterization information obtained via a different imaging modality, such as CT imaging. FIG. 3 shows a process for fusing TC information and still frames of ultrasound image data. FIG. 4 shows a process for fusing TC information and sequential frames (e.g., loops) of ultrasound image data. The TC information may be fused with the ultrasound image data according to the method of FIG. 5. Example images of fused ultrasound image data and TC information are shown in FIGS. 6A-6C.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic wave. In this way, transducer elements 104 may convert electronic transmit signals into acoustic transmit beams.

After the elements 104 of the probe 106 emit pulsed ultrasonic signals into a body (of a patient), the pulsed ultrasonic signals reflect from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data.

The echo signals produced by transmit operation reflect from structures located at successive ranges along the transmitted ultrasonic beam. The echo signals are sensed separately by each transducer element and a sample of the echo signal magnitude at a particular point in time represents the amount of reflection occurring at a specific range. Due to the differences in the propagation paths between a reflecting point P and each element, however, these echo signals are not detected simultaneously. Receiver 108 amplifies the separate echo signals, imparts a calculated receive time delay to each, and sums them to provide a single echo signal which approximately indicates the total ultrasonic energy reflected from point P located at range R along the ultrasonic beam oriented at the angle θ.

The time delay of each receive channel continuously changes during reception of the echo to provide dynamic focusing of the received beam at the range R from which the echo signal is assumed to emanate based on an assumed sound speed for the medium.

Under direction of processor 116, the receiver 108 provides time delays during the scan such that steering of receiver 108 tracks the direction θ of the beam steered by the transmitter and samples the echo signals at a succession of ranges R so as to provide the time delays and phase shifts to dynamically focus at points P along the beam. Thus, each emission of an ultrasonic pulse waveform results in acquisition of a series of data points which represent the amount of reflected sound from a corresponding series of points P located along the ultrasonic beam.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the real RF (radio-frequency) data and generates complex data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec and/or may acquire volumetric data at a suitable volume rate. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates or volume rates that are considerably faster than 20 frames/sec (or volumes/sec) while other embodiments may have real-time frame-rates or volume rates slower than 7 frames/sec (or volumes/sec). The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate or volume rate of, for example, 10 Hz to 30 Hz (e.g., 10 to 30 frames per second). Images generated from the data (which may be 2D images or 3D renderings) may be refreshed at a similar frame-rate on display device 118. Other embodiments may acquire and display data at different rates. For example, some embodiments may acquire data at a frame-rate or volume rate of less than 10 Hz or greater than 30 Hz depending on the size of the frame and the intended application. A memory 120 is included for storing processed frames or volumes of acquired data. In an exemplary embodiment, the memory 120 is of sufficient capacity to store at least several seconds' worth of frames or volumes of ultrasound data. The frames or volumes of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines, frames, and/or volumes are stored in memory and may include timing information indicating a time at which the image lines, frames, and/or volumes were stored in memory. The modules may include, for example, a scan conversion module to perform scan conversion operations to convert the acquired data from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional or three-dimensional ultrasound scan, a block of data (which may be two-dimensional or three-dimensional) comprising scan lines and their samples is generated. After back-end filters are applied, a process known as scan conversion is performed to transform the data block into a displayable bitmap image with additional scan information such as depths, angles of each scan line, and so on. During scan conversion, an interpolation technique is applied to fill missing holes (i.e., pixels) in the resulting image. These missing pixels occur because each element of the block should typically cover many pixels in the resulting image. For example, in current ultrasound imaging systems, a bicubic interpolation is applied which leverages neighboring elements of the block. As a result, if the block is relatively small in comparison to the size of the bitmap image, the scan-converted image will include areas of less than optimal or low resolution, especially for areas of greater depth.

Figure 2:
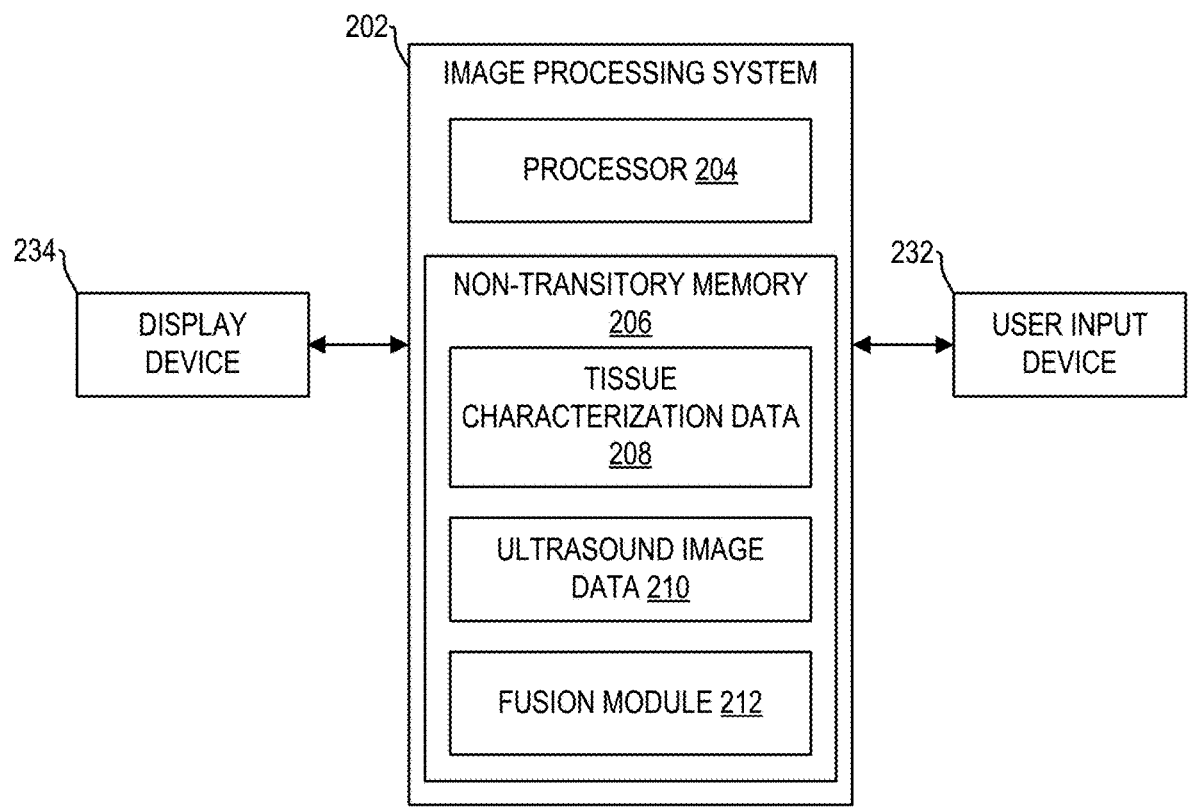
FIG. 2 is a block diagram showing an example image processing system.

Referring to FIG. 2, an image processing system 202 is shown, in accordance with an exemplary embodiment. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing system 202 is included in a device (e.g., edge device, server, etc.) communicably coupled to the ultrasound imaging system via wired and/or wireless connections. In some embodiments, at least a portion of image processing system 202 is included in a separate device (e.g., a workstation), which can receive ultrasound data (such as images and/or 3D volumes) from the ultrasound imaging system or from a storage device which stores the images/data generated by the ultrasound imaging system. Image processing system 202 may be operably/communicatively coupled to a user input device 232 and a display device 234. In one example, the user input device 232 may comprise the user interface 115 of the ultrasound imaging system 100, while the display device 234 may comprise the display device 118 of the ultrasound imaging system 100.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store TC data 208, ultrasound image data 210, and a fusion module 212. The TC data 208 may include medical image data (e.g., 2D images, 3D renderings, and/or volumetric datasets) acquired with non-ultrasound imaging modalities, such as computed tomography (CT) images, magnetic resonance (MR) images, PET images, SPECT images, X-ray images, or the like. The non-ultrasound medical image data may include TC information that characterizes/identifies aspects of the anatomical features present in the non-ultrasound medical images. For example, CT images may differentiate among various tissue types such as fat and muscle as well as depict degrees of perfusion, fibrosis, edema, hemorrhage, and tissue affected by diseases such as amyloidosis or Fabry disease. The medical images included in the TC data 208 may be processed to visually depict desired TC information, such as fat being visualized in a first color and muscle being visualized in a second color, at least in some examples. In other examples, the TC information present in the medical images of the TC data 208 may be visualized via varying levels of image brightness. The ultrasound image data 210 may include 2D images and/or 3D volumetric data, from which 3D renderings and 2D images/slices may be generated, captured by the ultrasound imaging system 100 of FIG. 1 or another ultrasound imaging system. The ultrasound image data 210 may include B-mode images, Doppler images, color Doppler images, M-mode images, etc., and/or combinations thereof.

Figure 5:
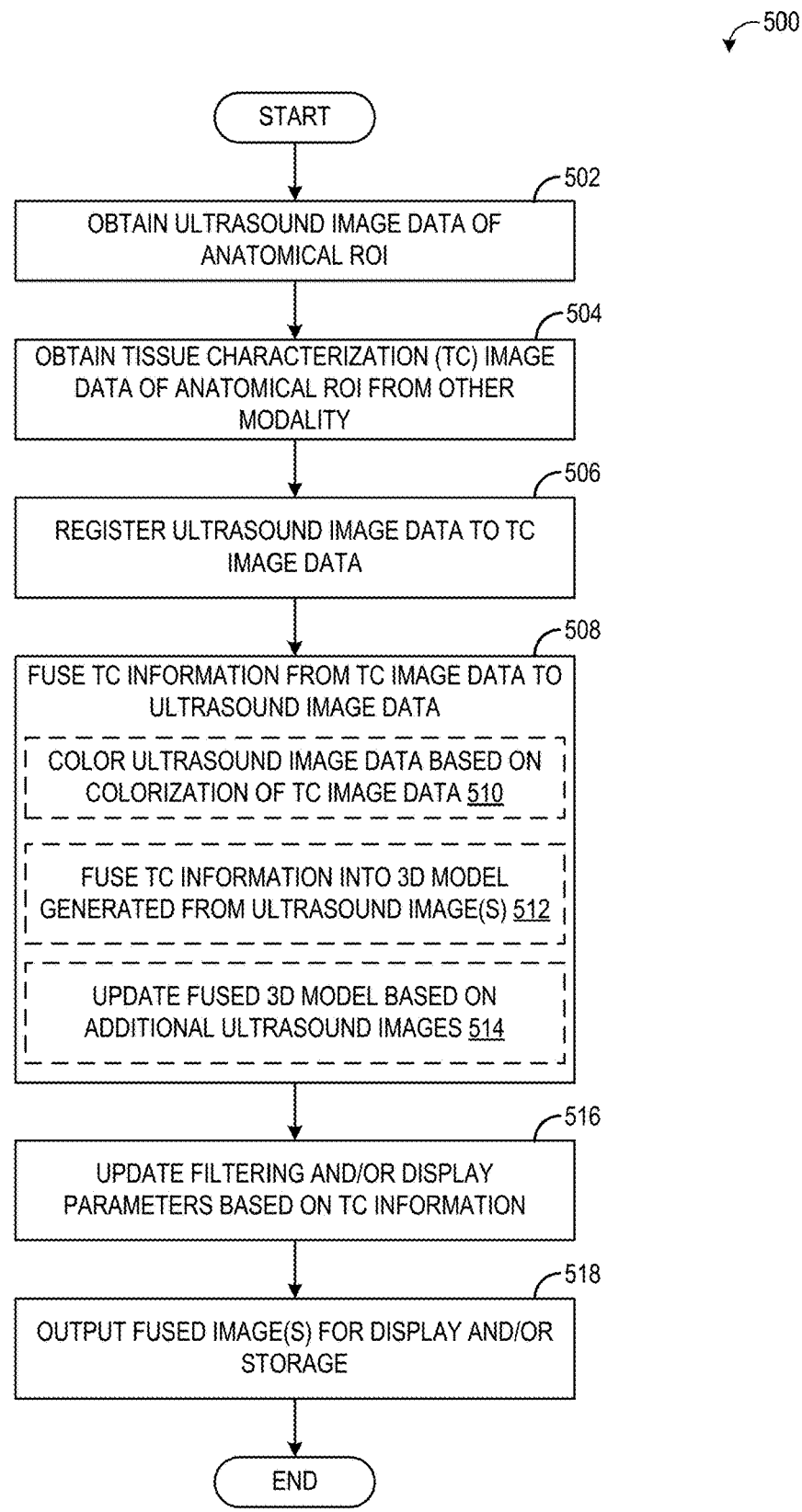
FIG. 5 is a flow chart illustrating a method for fusing TC information with ultrasound image data.
Figure 6A:
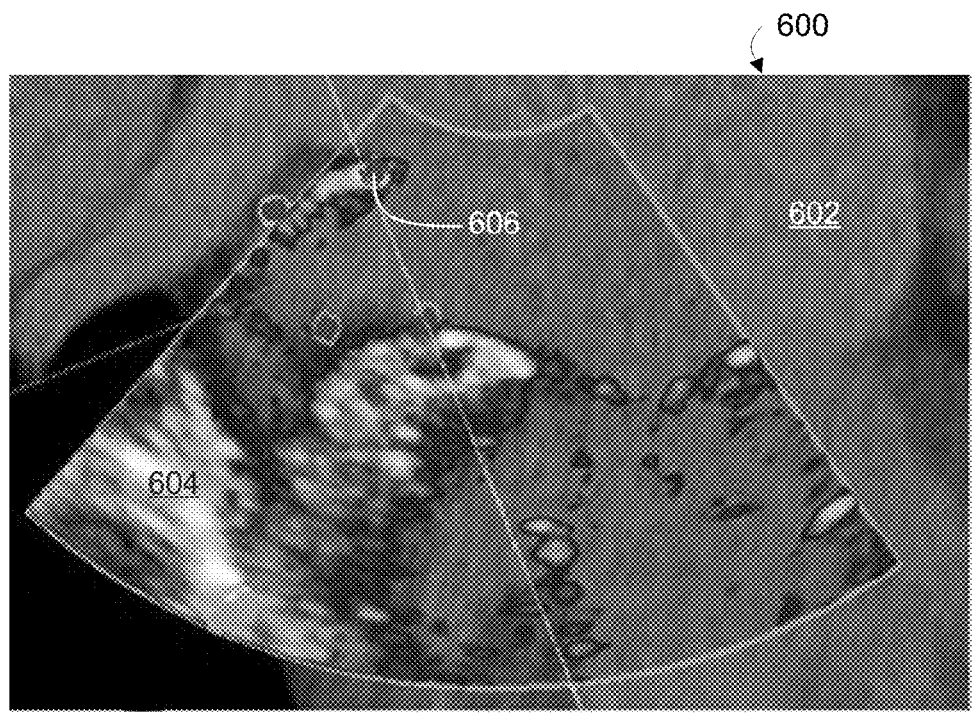
FIGS. 6A-6C show example fused images.
Figure 6B:
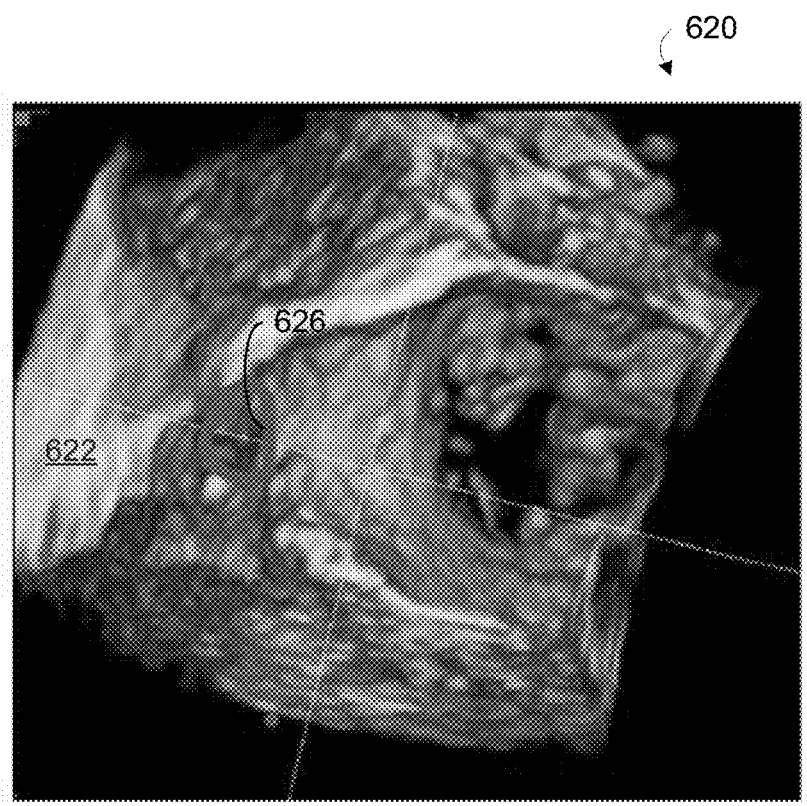
Figure 6C:
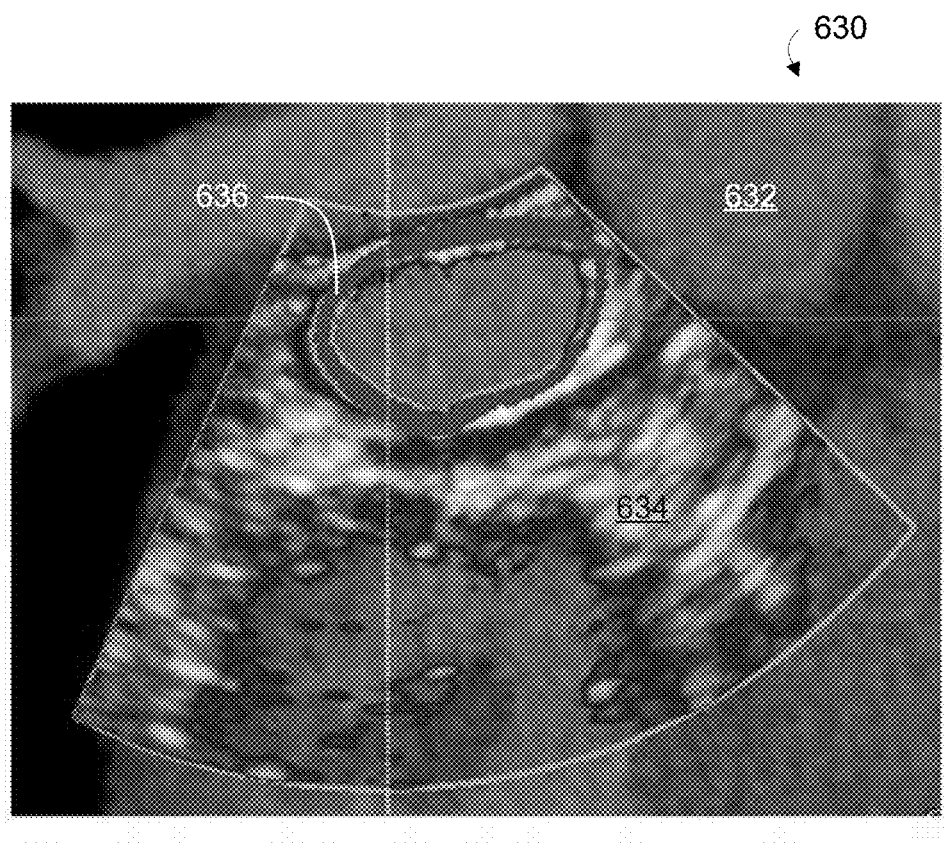

The fusion module 212 may comprise machine-readable instructions that may be executed (e.g., by processor 204) to carry out one or more methods, such as method 500 of FIG. 5, to visualize the TC data 208 and the ultrasound image data 210 simultaneously. The fusion module 212 may be used to generate and store fused images including both TC data and ultrasound imagery. As described in more detail below, the fusion module 212 may register ultrasound image data of an anatomical region of a patient of the ultrasound image data 210 with corresponding non-ultrasound image data of the anatomical region of the patient from another modality (e.g., stored in the TC data 208), such as by identifying landmarks within the tissue in both the ultrasound image data 210 and the TC data 208 and applying a transfer function, affine matrix, or another suitable function in order to align, resize, or otherwise adjust one or both of the ultrasound image data and non-ultrasound image data. Once the images and/or data volumes are registered, TC information from the non-ultrasound image data may be fused with the ultrasound image data, so that the TC information is applied to any subsequent ultrasound images. The fused images generated by the fusion module may therefore include both anatomical feature information and TC data. The output of the fusion module may be stored within non-transitory memory 206 and/or visualized through the use of a display device 234.

In some embodiments, the non-transitory memory 206 may include components included in two or more devices, which may be remotely located and/or configured for coordinated processing. For example, at least some of the images stored as part of the TC data 208 may be stored in an image archive, such as a picture archiving and communication system (PACS). In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image and a non-ultrasound tissue characterization image for fusion via the fusion module 212.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

FIG. 3 schematically illustrates a pipeline 300 for creating fused 3D renderings and slices comprising both ultrasound and TC data. Pipeline 300 takes as input TC data, visualized herein as a TC image 302, which is a non-limiting example of the TC data 208 stored in the non-transitory memory 206. TC image 302 may include an anatomical ROI of a patient, which in the current example is a heart. In the current example, the TC image 302 is a CT image obtained from a CT imaging system. It should be noted that CT images/projection data provide a non-limiting example of a n n-ultrasound modality with which the TC data may be acquired. TC data may be sourced from other modalities, such as PET scans or MRI scans. In the example of CT scans, TC data may be obtained by reconstructing one or more images from a sinogram (e.g., projection data) or generating a 3D model from the projection data. To generate a representation of the TC data, such as the false-color photograph of the TC image 302 with TC data, color may be added depending on, for example, the Hounsfield scale (HU) values of each point in the image(s) or model. In the example shown in FIG. 3, TC image 302 is colored so that a first tissue type (e.g., myocardial scar or fibrous tissue) is shown in a first color (e.g., purple), a second tissue type (e.g., normal myocardium) is shown in a second color (e.g., yellow/gold), etc. While a single TC image depicting a surface of a 3D model of a heart generated from projection data is shown, it is to be appreciated that the TC data may be obtained from a 3D volume of data.

Pipeline 300 also takes as input ultrasound image data 304 of the anatomical ROI of the patient. Thus, the ultrasound image data are of the same anatomical ROI (e.g., the heart) of the same patient as the TC image 302. The ultrasound image data 304 may include 3D renderings of volumetric data, such as 3D ultrasound rendering 305, and/or slices (e.g., 2D images) obtained from the volumetric data, such as slices 2D ultrasound slices 307. The 3D ultrasound renderings and slices may be acquired with a suitable ultrasound imaging system, such as the ultrasound probe 106 of FIG. 1, which may acquire volumetric ultrasound data from which the 3D renderings and slices may be generated. The volumetric ultrasound data may include voxel data where each voxel is assigned a value and an opacity. The value and opacity may correspond to the intensity of the voxel.

The 3D ultrasound rendering 305 may be a non-limiting example of the ultrasound image data 210 stored in the non-transitory memory 206. The 3D ultrasound rendering 305 may be generated, for example, through the use of traditional 3D ultrasound reconstruction techniques. One or more 2D ultrasound slices 307 may be generated from the volumetric ultrasound data, such as short axis, long axis, 2-chamber, and 4-chamber slices. The volumetric ultrasound data may be used to produce a coloring of both the 3D ultrasound rendering 305 and the 2D ultrasound slices 307. The example 3D ultrasound rendering 305 shown is colored to highlight the anatomy of the imaged ROI. For example, the coloring shown in the 3D ultrasound rendering may represent depth, such that structures closer to the viewing plane are colored bright orange/yellow while structures further from the viewing plane are colored darker and in a gray and/or bluish tone. Additionally, shadows from an artificial light source may result in darker colors in shadowed regions. Similarly, the brightness of the pixels within the 3D ultrasound rendering 305 may be given by the intensity of echoes returned to the ultrasound probe. The 2D ultrasound slices 307 are also generated from the volumetric ultrasound data; coloration and brightness is specified in a similar way to the 3D ultrasound rendering 305.

First image data, which may be the TC image 302, may be registered and fused with second image data, e.g., the volumetric ultrasound data, the 3D ultrasound rendering 305, and/or 2D ultrasound slices 307, at 306. The registration and fusion process may be performed via executable instructions on the processor 204 of the image processing system 202 using instructions stored in the fusion module 212. The registration may include identifying overlapping anatomy imaged in the ultrasound image data 304 and the TC image 302 and adjusting a size, orientation, scale, etc., of the TC image 302 to match the size, orientation, scale, etc., of the corresponding anatomy in the ultrasound image data 304. The registration process may also include generating and storing a mathematical transformation describing the rotation, scaling, etc., used to translate points in one scan to another. The transformation may be applied to other points within the anatomical ROI, allowing for the remaining points to be identified. Additionally or alternatively, registration may include identifying a feature of an anatomical ROI (e.g., a surface of the heart) in the volumetric ultrasound data and in the 3D data of the non-ultrasound modality (e.g., a model generated from the projection data and/or from a plurality of images reconstructed from the projection data of the CT imaging system) and registering the volumetric ultrasound data of the anatomical ROI to the 3D data of the anatomical ROI of the non-ultrasound modality. Fusion may be accomplished through mapping the TC data onto a 3D model generated by the ultrasound image data. For example, the first tissue colored with the first color in the TC image 302 may be mapped to the corresponding voxels or pixels of the 3D rendering and/or one or more slices based on the registration, and the voxels or pixels of the 3D rendering and/or slices may be colored with the first color. Details about the fusion and registration process are disclosed in FIG. 5.

The registration and fusion performed at 306 of the first image data (e.g., the TC image 302) with the second image data (e.g., the 3D ultrasound rendering 305) may yield fused 3D ultrasound image data 308. The fused 3D ultrasound image data 308 may include a fused 3D rendering 309 and/or one or more fused slices 311. The fused slices 311 may be sourced from the volumetric ultrasound data and the color and/or brightness of the fused slices 311 may be adjusted according to the TC data, e.g. the TC image 302, according to the registration and fusion performed at 306. The coloration within the TC data may also be adjusted volumetrically, allowing for the voxels and/or pixels of the TC image 302 to be used to adjust the color and/or brightness of the pixels and/or voxels of the ultrasound data. The fused 3D rendering 309 and the fused slices 311 each represent the same anatomy as the corresponding 3D ultrasound rendering 305 or 2D ultrasound slices 307, with color and/or brightness adjusted based on the TC data. Method 306 may also output the fused volumetric data itself as, for example, a 3D model. For example, in the fused 3D rendering 309 and upper left corner slice of the fused slices 311, the coloring is a mix of the TC coloring and the depth coloring (e.g., as shown in the 3D rendering 305). The mixing or blending of the color for a given anatomical position could for example be additive or subtractive. In the example in the fused 3D rendering 309, additive mixing causes the colors to mainly be reflecting the TC coloring, with purple indicating scar or fibrous tissue and orange indicating normal myocardium. While coloring the ultrasound images based on the TC data is shown and described herein, other material properties could be assigned to the voxel to be used in the rendering algorithm, e.g. changing the coloring, texture, reflection, etc.

Thus, pipeline 300 shows how tissue characterization data may be fused with ultrasound renderings or slices to visually represent desired tissue characterization information in an ultrasound image, at a single point in time. As described in FIG. 4 below, a plurality of additional ultrasound images may form an animated loop (e.g. representing a bodily process, such as the cardiac cycle). The additional ultrasound images may be used to update a fused 3D model so that a loop of ultrasound images (e.g., a cine loop) obtained across multiple points in time may include tissue characterization information.

FIG. 4 shows a pipeline 400 to generate renderings, slices, and loops of fused imagery. The pipeline 400 may take as input three sources: ultrasound data, such as one or more 3D ultrasound image(s) 404 (which may represent volumetric ultrasound data), a CT image with TC data (herein represented by a TC image 402), and a 3D ultrasound image (or volume) loop 412. As noted before, the CT imagery provides a non-limiting example of TC data. TC data input to pipeline 400 may include volumetric tissue characterization data. In the example TC image 402 shown, a rendering of the heart is shown with various colors corresponding to different types of tissue (e.g., normal myocardium and scar tissue).

The TC image 402 is a non-limiting example of a first image used for coloring of one or more second images. In the example image shown, a false coloring is provided to show different types of tissue detected within the imaged anatomical ROI. For example, the purple color represents a first type of tissue (e.g., scar tissue) and the red/orange color represents a second type of tissue (e.g., normal tissue).

The ultrasound data represented by the 3D ultrasound image(s) 404 may be registered and fused with the tissue characterization data at 406. The registration and fusion of the TC data at 406 is similar to the registration and fusion of TC data in at 306 of FIG. 3: both methods serve to identify common regions within the ultrasound and TC scans and fuse the two images together. More details about the registration process are given below with respect to FIG. 5. As detailed further with respect to FIG. 5, the TC characterization image data may be scaled, translated and/or rotated to fit the 3D ultrasound images/volumetric data.

The 3D ultrasound image data may also be used to create a 3D model 408 of the underlying anatomy. The 3D model may be created from volumetric ultrasound data (from which a plurality of 3D ultrasound images may be generated, as shown). The 3D model 408 may contain voxel data, which may be used to represent the intensity of reflected ultrasound waves by the opacity of each voxel. In other examples, the 3D model 408 may be a surface model and thus may include surface points rather than voxels. In the embodiments disclosed herein, the 3D model is generated independently of any TC data.

The registered and fused 3D data generated in 406 may be applied to the 3D model 408 to generate a fused 3D model 410. The fused 3D model 410 may therefore contain both 3D structural information gathered from ultrasound image data and TC data gathered from a CT image or volume. The fused 3D model 410 may be created by updating the coloring, opacity, and/or brightness of the volumetric data (e.g., voxels or surface points) of the 3D model 408 generated via ultrasound images.

Given the fused 3D model 410 and a 3D ultrasound image loop 412, an updated fused 3D model 414 may be generated each time a new ultrasound image (or volume) is obtained. The 3D ultrasound image loop 412 may comprise a plurality of 3D ultrasound images, each similar to the 3D ultrasound image 404. The loop may represent, for example, a series of ultrasound scans acquired at different points in time. For example, the loop may represent images or volumes taken at different phases of a patient's cardiac cycle. In other examples, the 3D ultrasound image loop 412 may be acquired during interventional procedures.

Each updated fused 3D model 414 may be generated, for example, by adjusting the fused 3D model 410 based on the 3D images within the 3D ultrasound image loop 412. In one embodiment, the voxels or surface points of the fused 3D model may be adjusted (e.g., opacity, color) according to each image within the 3D ultrasound image loop 412.

The updated fused 3D models 414 may be used to generate a plurality of fused 3D images, forming a fused 3D ultrasound image loop 416 (e.g., including 3D renderings). Since the updated fused 3D models 414 each contain volumetric ultrasound and TC data, the coloration of the updated fused 3D models 414 may be used to adjust the coloration and/or brightness of the images within the 3D ultrasound image loop 412 to form the fused 3D ultrasound image loop 416. The volumetric data contained in the updated fused 3D models 414 may also be used to generate slices of the fused 3D ultrasound rendering 418. The slices of the fused 3D ultrasound rendering 418 may also be independently viewed and/or stored to non-transitory memory.

Turning now to FIG. 5, it shows a flow chart illustrating an example method 500 for registering and generating fused ultrasound images. Method 500 is described with regard to the systems and components of FIGS. 1-2, though it should be appreciated that the method 500 may be implemented with other systems and components without departing from the scope of the present disclosure. Method 500 may be carried out according to instructions stored in non-transitory memory of a computing device, such as memory 120 of FIG. 1 or non-transitory memory 206 of FIG. 2, and executed by a processor of the computing device, such as processor 116 of FIG. 1 or processor 204 of FIG. 2. Method 500 may be employed to generate the fused imagery created in pipeline 400 and in pipeline 300.

At 502, method 500 includes obtaining ultrasound image data of an anatomical region of interest (ROI) of a patient. The anatomical ROI may include anatomical features to be imaged, such as, for example, the heart. In some examples, volumetric ultrasound data may be obtained from which 3D renderings of the volumetric ultrasound data and/or 2D slices may be generated. The ultrasound image data obtained at 502 may include black-and-white/grayscale images of the anatomical ROI, each comprising a grid of pixels. The brightness of each pixel may represent the strength of an echo returned to the ultrasound probe. In some examples, the ultrasound image(s) may be colored to show certain features, such as depth. An ultrasound system (e.g. the system of FIG. 1) may be used to perform sweeps of the anatomical ROI and use the data collected to generate a 3D, volumetric dataset of the region imaged. The volumetric data may be viewed in a number of ways, such as 3D renderings and slices. The volumetric rendering may also include voxel data or surface point data, where the intensity of each voxel or surface point is specified by the intensity of the ultrasound reflections received by the probe At 504, method 500 includes obtaining tissue characterization (TC) image data of the anatomical ROI of the patient from another modality. The other modality may be, as a non-limiting example, a CT imaging system. The TC image data may comprise a grid of pixels, a volume of voxels, or another suitable representation (e.g., surface model), which include TC data such as false color corresponding to the characterization of the tissue being imaged. At 506, the ultrasound image data obtained at 502 is registered to the TC image data obtained at 504. The registration process may comprise identifying noteworthy anatomical points in both the ultrasound image data and the TC image data and aligning, resizing, reorienting, etc., the ultrasound image data and TC image data based on the anatomical points. Noteworthy points may include, for example, boundaries between different types of tissues, easily-identifiable points within organs, surfaces of organs, and/or other points. Registering the ultrasound image data and the TC image data may include registering images, such that each pixel of an ultrasound image is associated with a respective pixel of a TC image. In other examples, volumetric data/models of the anatomical ROI may be registered, such that each voxel of an ultrasound volumetric dataset or surface point of a 3D ultrasound model is associated with a respective voxel of a TC volumetric dataset of surface point of a 3D TC model.

At 508, the TC information from the TC image data is fused to the ultrasound image data, to create one or more fused ultrasound images. Fusing the TC information to the ultrasound image data may include, as indicated at 510, coloring an ultrasound image generated from the ultrasound image data based on the colorization of the TC image data. Coloring the ultrasound image includes identifying one or more first pixels, voxels, or model points (e.g., surface points) of the TC image data having a first tissue characteristic based on a first color and/or brightness of the one or more of the first pixels, voxels, or model points and adjusting a color and/or a brightness of one or more corresponding first pixels of the ultrasound image to match the first color and/or brightness of the first pixels, voxels, or model points of the TC image data. The process may be repeated for each additional tissue characteristic conveyed by the TC image data, e.g., one or more second pixels, voxels, or model points having a second color or brightness may be identified and any corresponding pixels in the ultrasound image may be adjusted to have the second color and/or brightness. It should be appreciated that instead of adjusting the ultrasound image to have a colorization that matches the colorization of the TC information, the ultrasound image may be adjusted to have a different color scheme than the colorization of the TC information and/or the ultrasound image may be adjusted to have different texture, transparency, reflection, etc., though the pixels of the ultrasound image that are adjusted may be selected based on the TC information. Further, while generating an ultrasound image and then adjusting one or more pixels of the ultrasound image has been described herein, in some examples a volumetric dataset or 3D model generated from the ultrasound image data may be adjusted based on the TC information, and then one or more ultrasound images may be generated from the fused/adjusted volumetric dataset or 3D model.

Fusing the TC information to the ultrasound image data may include, as indicated at 512, fusing TC information into a 3D model generated from the ultrasound image data. The ultrasound image data obtained at 502 may be volumetric data that may be used to generate a 3D model of an anatomical ROI, such as the heart. The TC information may be fused with the 3D model, for example, by adjusting a color and/or brightness of the voxels within the 3D model or surface points of the 3D model using the volumetric TC data (e.g., voxels or surface points of the 3D model that correspond to voxels of surface points of the TC image data may colored or otherwise adjusted based on the coloring of the voxels or surface points of the TC image data). The fused 3D model 410 is a non-limiting example of the result of fusing TC information into a 3D model generated from ultrasound images as performed at 512.

At 514, the fused 3D model generated at 512 may be updated based on additional ultrasound images. The additional images may be sourced from, for example, a plurality of images in a 3D ultrasound image loop, such as the 3D ultrasound image loop 412 of FIG. 4. The 3D ultrasound image loop may be used to generate a plurality of 3D models based on the ultrasound data of each image. Each such 3D model may be identified with the anatomy of the 3D image obtained in 502, allowing for the fused 3D model generated at 512 to be updated. Updating may comprise, for example, stretching or transforming the fused 3D model to match the 3D models sourced from the additional ultrasound images. Stretching and transforming of the fused 3D model may therefore allow the TC data to be correspondingly mapped.

At 516, filtering and/or display parameters of ultrasound images may be updated based on the TC information. Updating the filtering information may comprise taking as input the TC information to generate a filter based on HU values. Filtering may be performed in the image domain and/or the spatial frequency domain. Display parameters may include image compression, gamma correction, or normalizing the brightness of an on-screen image. For example, the sharpness of the ultrasound rendering may be adjusted to emphasize tissues or calcified regions. Tissues and calcified images may be readily identified through the CT imagery. Medical intervention planning information may also be added to fused images by manually applying ("burning in") coloring to the TC data. In some examples, a specific HU value (e.g. 3000 HU) may be used to differentiate the burned in regions, which may serve as annotations for medical professionals. Burned in locations within the TC data may therefore be visible within the fused imagery.

At 518, one or more fused images are output for display and/or storage in memory. The output images generated in step 518 may be stored in the non-transitory memory 206 of the image processing system 202. Images may also be output to the display device 234, where the fused imagery may be viewed by an operator. The operator may interact with the stored images via a user input device 232.

FIGS. 6A-6C show example images generated through the fusion of ultrasound and CT imagery. Registration is performed to register the ultrasound and CT image data using the same or similar registration techniques as discussed above with respect to FIGS. 3-5, such as through scaling, rotating, and/or translating the ultrasound image data to match the underlying anatomy of the CT image data within an anatomical ROI. FIGS. 6A and 6C each show slices of volumetric ultrasound data of a ROI (e.g., a heart) while FIG. 6B shows a 3D rendering of the ROI.

FIG. 6A shows an image 600 containing both CT image data 602 (shown in gray) and ultrasound data 604, shown in yellow and bounded by a blue fan shape. In this example, the ultrasound data 604 is superimposed on top of the CT image data 602. In order to form image 600, the ultrasound data 604 was rotated, translated, and/or scaled in order to align the underlying anatomy within the ROI. Overlaying the ultrasound imagery and the CT imagery allows for the points within each image to be registered with one another. Registration of the images in this way allows for registration of the other pixels and/or voxels within the images, which may in turn be used in the generation of fused 3D imagery.

FIG. 6A also shows four burned-in areas, such as the area 606. Burned-in areas are areas wherein the CT images have been edited to mark areas where imaging, interventional procedures, or other notable regions are planned. CT images may be edited, for example, by medical professionals by way of changing the HU values within the images, as a way to annotate the image in preparation of an interventional procedure or planned imaging. In this case, since the coloration is saved on the CT image data, the burned-in areas may also be viewed when the color of the ultrasound imagery is adjusted based on the CT image data. In the present example, the burned-in areas (which may appear as bright regions in the CT image data) may be transformed into red areas in the ultrasound image data.

FIG. 6B shows a volumetric rendering 620 of fused ultrasound and TC data, where the TC data is obtained from the CT image data as explained above with respect to FIG. 6A. Volumetric ultrasound data 622 is represented here by surface points (or voxel information) and viewed from a given perspective. The surface points of the underlying ultrasound are colored in different shades of yellow and blue, corresponding to depth, as well as shadows from an artificial light source. Volumetric rendering 620 also includes adjustments to the coloration of the volumetric ultrasound data 622 based on TC data present in the CT image data. In this case, a burned-in area 626 is specified in the CT image data, then rendered onto/fused with the volumetric ultrasound data 622 and shown in the volumetric rendering 620. The red coloration represents a specific HU value of the CT image data, as explained above with respect to FIG. 6A. The burned-in area 626 is the same burned-in area as the burned-in areas of FIG. 6A, shown on the surface of the ROI as opposed to a slice through the ROI shown in FIG. 6A. Although the burned-in areas, such as the burned-in area 626, represent adjustments to colorization from TC data, other color adjustments may be performed on the image, such as adjusting a texture, reflectance, etc., in the image dependent on the TC information. In the volumetric rendering 620, the coloration is sourced from ultrasound, except in areas affected by burned-in CT data.

3D ultrasound models, such as a 3D model used to generate volumetric rendering 620, may also be updated through the use of a plurality of additional ultrasound images to form a series of 3D models, e.g. within a loop of real-time ultrasound data. Color and/or brightness adjustments sourced from the CT data may therefore move along with the model, as regions of corresponding anatomy may be registered and updated.

FIG. 6C shows a slice 630 of the same volumetric data used to generate the volumetric rendering 620. Slice 630 contains CT image data 632, shown in black and white. Ultrasound data 634 is superimposed, with regions of identical anatomy identified and registered within the image. The slice 630 shows a burned-in area 636 of burned-in CT data used as an annotation. The burned-in area 636 also appears within the ultrasound data 634 superimposed onto the CT image data 632, since the two modalities are being used to simultaneously show different information within the same anatomical ROI. The burned-in area 636 is a non-limiting example of adjusting the color and/or brightness of the ultrasound data 634, based on CT image data 632. A plurality of such slices may be assembled to create a volumetric rendering featuring both the TC data and the ultrasound data simultaneously.

A technical effect of fusing tissue characterization information and ultrasound imaging data is that the tissue characterization information may be seen within the ultrasound imaging data without requiring side-by-side image display, thus easing the cognitive load of a user viewing the tissue characterization information and ultrasound imaging data.

The disclosure also provides support for a method, comprising: obtaining first image data of an anatomical region of interest (ROI) of a patient, the first image data including tissue characterization information and acquired with a first imaging modality, obtaining second image data of the anatomical ROI of the patient, the second image data acquired with a second imaging modality, registering the first image data and the second image data, adjusting the second image data based on the tissue characterization information and the registration, wherein the adjusting includes filtering, adjusting colorization, adjusting brightness, and/or adjusting material appearance properties of one or more aspects of the second image data, generating a fused image from the adjusted second image data, and outputting the fused image for display and/or storage. In a first example of the method, the second image data comprises ultrasound image data and the first image data comprises non-ultrasound image data. In a second example of the method, optionally including the first example, the first image data comprises computed tomography image data. In a third example of the method, optionally including one or both of the first and second examples, registering the first image data and the second image data comprises associating each voxel of the first image data with a respective voxel of the second image data. In a fourth example of the method, optionally including one or more or each of the first through third examples, adjusting the second image data based on the tissue characterization information and the registration comprises: identifying one or more first voxels of the first image data having a first tissue characteristic based on a color and/or brightness of the one or more first voxels, identifying one or more second voxels of the second image data that correspond to the one or more first voxels based on the registering, and adjusting the one or more second voxels of the second image data in correspondence with the color and/or brightness of the one or more first voxels. In a fifth example of the method, optionally including one or more or each of the first through fourth examples, registering the first image data and the second image data and adjusting the second image data based on the tissue characterization information and the registration comprises generating a 3D model of the anatomical ROI from the first image data and adjusting one or more aspects of the 3D model based on the tissue characterization information to generate a fused 3D model. In a sixth example of the method, optionally including one or more or each of the first through fifth examples, the method further comprises: updating the fused 3D model as additional first image data is acquired.

The disclosure also provides support for a system, comprising: a processor, and non-transitory memory storing instructions executable by the processor to: obtain first image data of an anatomical region of interest (ROI) of a patient, the first image data including tissue characterization information and acquired with a first imaging modality, obtain second image data of the anatomical ROI of the patient, the second image data acquired with a second imaging modality, register the first image data and the second image data, adjust a color and/or a brightness of one or more aspects of the second image data based on the tissue characterization information and the registration, generate a fused image from the adjusted second image data, and output the fused image for display and/or storage. In a first example of the system, the second imaging modality comprises ultrasound imaging. In a second example of the system, optionally including the first example, the first imaging modality comprises computed tomography imaging. In a third example of the system, optionally including one or both of the first and second examples, registering the first image data and the second image data comprises registering a tissue characterization image with an image generated from the second image data, wherein registering the tissue characterization image and the image includes associating each pixel of the tissue characterization image with a respective pixel of the image. In a fourth example of the system, optionally including one or more or each of the first through third examples, adjusting a color and/or a brightness of one or more aspects of the second image data based on the tissue characterization information and the registration comprises: identifying one or more first pixels of the tissue characterization image having a first tissue characteristic based on a color and/or brightness of the one or more first pixels, identifying one or more pixels of the image that correspond to the one or more first pixels based on the registering, and adjusting the color and/or brightness of the one or more pixels of the image in correspondence with the color and/or brightness of the one or more first pixels to form the fused image. In a fifth example of the system, optionally including one or more or each of the first through fourth examples, registering the first image data and the second image data comprises registering voxels of the first image data with voxels of the second image data. In a sixth example of the system, optionally including one or more or each of the first through fifth examples, adjusting a color and/or a brightness of one or more aspects of the second image data based on the tissue characterization information and the registration comprises: identifying one or more first voxels of the first image data having a first tissue characteristic based on a color and/or brightness of the one or more first voxels, identifying the one or more second voxels of the second image data as voxels that correspond to the one or more first voxels based on the registering, and adjusting the color and/or brightness of the one or more second voxels of the second image data in correspondence with the color and/or brightness of the one or more first voxels.

The disclosure also provides support for a method, comprising: obtaining first image data of an anatomical region of interest (ROI) of a patient, the first image data including tissue characterization information, obtaining ultrasound image data of the anatomical ROI of the patient, building a 3D model based on the ultrasound image data, adjusting the 3D model based on the tissue characterization information to form a fused 3D model, generating one or more fused ultrasound images from the fused 3D model, and outputting the one or more fused ultrasound images for display and/or storage. In a first example of the method, the ultrasound image data is first ultrasound image data and further comprising obtaining second ultrasound image data, adjusting the fused 3D model based on the second ultrasound image data, generating one or more additional fused ultrasound images from the adjusted fused 3D model, and outputting the one or more additional fused ultrasound images for display and/or storage. In a second example of the method, optionally including the first example, the second ultrasound image data is acquired at a later point in time than the first ultrasound image data. In a third example of the method, optionally including one or both of the first and second examples, the one or more fused ultrasound images comprise one or more 3D renderings and/or one or more 2D images. In a fourth example of the method, optionally including one or more or each of the first through third examples, the tissue characterization information is conveyed in the first image data by a color and/or brightness of each voxel of the first image data. In a fifth example of the method, optionally including one or more or each of the first through fourth examples, adjusting the 3D model based on the tissue characterization information comprises adjusting a color and/or brightness of one or more voxels or surface points of the 3D model in correspondence to a color and/or brightness of each voxel of surface point of the first image data.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
   obtaining first image data of an anatomical region of interest (ROI) of a patient, the first image data including tissue characterization information and acquired with a first imaging modality;
   obtaining second image data of the anatomical ROI of the patient, the second image data acquired with a second imaging modality;
   registering the first image data and the second image data;
   adjusting the second image data based on the tissue characterization information and the registration, wherein adjusting includes adjusting a color of one or more voxels of the second image data based on a brightness of one or more corresponding voxels of the first image data, the one or more voxels of the first image data representing a burned-in area wherein the brightness of the one or more corresponding voxels was adjusted by a user;

generating a fused image from the adjusted second image data;

and outputting the fused image for display and/or storage.

2. The method of claim 1, wherein the second image data comprises ultrasound image data and the first image data comprises non-ultrasound image data.

3. The method of claim 1, further comprising generating a 3D model of the anatomical ROI from the second image data, wherein registering the first image data and the second image data and adjusting the second image data based on the tissue characterization information and the registration comprises registering the first image data to the 3D model and adjusting one or more voxels of the 3D model to generate a fused 3D model, and wherein generating the fused image from the adjusted second image data comprises generating the fused image from the fused 3D model.

4. The method of claim 2, wherein the first image data comprises computed tomography image data.

5. The method of claim 4, wherein registering the first image data and the second image data comprises associating each voxel of the first image data with a respective voxel of the second image data.

6. The method of claim 5, wherein adjusting the color of the one or more voxels of the second image data based on the brightness of the one or more corresponding voxels of the first image data comprises:

identifying the one or more corresponding voxels of the first image data having specific HU value or values;

identifying the one or more voxels of the second image data that correspond to the one or more corresponding voxels based on the registering;

and adjusting the color of the one or more voxels of the second image data based on the specific HU value or values.

7. The method of claim 3, further comprising updating the fused 3D model as additional second image data is acquired.

8. A system, comprising:

a processor;

and non-transitory memory storing instructions executable by the processor to:

obtain first image data of an anatomical region of interest (ROI) of a patient, the first image data including tissue characterization information and acquired with a first imaging modality; obtain second image data of the anatomical ROI of the patient, the second image data acquired with a second imaging modality; register the first image data and the second image data by identifying one or more anatomical landmarks in both of the first image data and the second image data, and aligning, resizing, and/or re-orienting one or both of the first image data and the second image data based on the one or more anatomical landmarks;

adjust a color of one or more pixels of the second image data based on the tissue characterization information and the registration to form a fused image, wherein adjusting the color of the one or more pixels includes adjusting the color of the one or more pixels based on a brightness of one or more corresponding pixels of the first image data, the one or more pixels of the first image data representing a burned-in area wherein the brightness of the one or more corresponding pixels was adjusted by a user;

and output the fused image for display and/or storage.

9. The system of claim 8, wherein the second imaging modality comprises ultrasound imaging.

10. The system of claim 8, wherein registering the first image data and the second image data comprises registering a tissue characterization image generated from the first image data with an image generated from the second image data, and wherein registering the tissue characterization image and the image includes associating each pixel of the tissue characterization image with a respective pixel of the image based on the one or more anatomical landmarks.

11. The system of claim 8, wherein registering the first image data and the second image data comprises registering pixels of the first image data with pixels of the second image data, and wherein the one or more anatomical landmarks include identifiable points within and/or on surfaces of organs.

12. The system of claim 9, wherein the first imaging modality comprises computed tomography imaging, and wherein the one or more anatomical landmarks include boundaries between different types of tissue.

13. The system of claim 10, wherein adjusting the color of the one or more pixels of the second image data based on the brightness of the one or more corresponding pixels of the first image data comprises:

identifying the one or more pixels of the first image data representing the burned-in area wherein the brightness of the one or more pixels was adjusted by the user;

identifying the one or more pixels of the second image data that correspond to the one or more corresponding pixels based on the registering;

and adjusting the color of the one or more pixels of the second image data to form the fused image.

14. A method, comprising:

obtaining first image data of an anatomical region of interest (ROI) of a patient, the first image data including tissue characterization information;

obtaining ultrasound image data of the anatomical ROI of the patient; building a 3D model based on the ultrasound image data;

adjusting the 3D model based on the tissue characterization information to form a fused 3D model, wherein the adjusting includes adjusting a color of one or more voxels of the 3D model based on a brightness of one or more corresponding voxels of the first image data, the one or more corresponding voxels of the first image data representing a burned-in area wherein the brightness of the one or more corresponding voxels was adjusted by a user;

generating one or more fused ultrasound images from the fused 3D model, outputting the one or more fused ultrasound images for display and/or storage;

obtaining second ultrasound image data;

adjusting the fused 3D model based on the second ultrasound image data, wherein adjusting the fused 3D model comprises at least one of stretching or transforming the fused 3D model based on the second ultrasound image data;

generating one or more additional fused ultrasound images from the adjusted fused 3D model;

and outputting the one or more additional fused ultrasound images for display and/or storage.

15. The method of claim 14, wherein the second ultrasound image data is acquired at a later point in time than the first ultrasound image data.

16. The method of claim 14, wherein the one or more fused ultrasound images comprise one or more 3D renderings and/or one or more 2D images.

17. The method of claim 14, wherein the tissue characterization information is conveyed in the first image data by a color and/or brightness of each voxel or surface point of the first image data.

18. The method of claim 14, wherein the brightness of the one or more corresponding voxels was adjusted by adjusting HU values of the one or more corresponding voxels.

* * * * *